(12) United States Patent  (10) Patent No.: US 8,677,602 B2
Dayton et al.  (45) Date of Patent: Mar. 25, 2014

(54) METHOD OF MAKING A FLEXIBLE DEVICE SHAFT WITH ANGLED SPIRAL WRAP

(75) Inventors: Peter L. Dayton, Brookline, MA (US); Michael P. Boutillette, Mountain View, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 18 days.

(21) Appl. No.: 13/357,676

(22) Filed: Jan. 25, 2012

(65) Prior Publication Data

US 2013/0023858 A1    Jan. 24, 2013

Related U.S. Application Data

(63) Continuation of application No. 12/546,599, filed on Aug. 24, 2009, now Pat. No. 8,124,876, which is a continuation of application No. 11/396,248, filed on Mar. 31, 2006, now Pat. No. 7,579,550.

(51) Int. Cl.
*B23P 13/00* (2006.01)
*H01B 7/17* (2006.01)

(52) U.S. Cl.
USPC .............................. 29/557; 174/108

(58) Field of Classification Search
USPC .............................. 29/557; 174/108
See application file for complete search history.

(56) References Cited

U.S. PATENT DOCUMENTS

| | | |
|---|---|---|
| 3,886,832 A * | 6/1975 | Harris ............................. 83/308 |
| 4,341,440 A | 7/1982 | Trezeguet |
| 4,580,551 A | 4/1986 | Siegmund |
| 4,669,172 A | 6/1987 | Petruzzi |
| 4,753,222 A | 6/1988 | Morishita |
| 4,791,966 A | 12/1988 | Eilentropp |
| 4,805,595 A | 2/1989 | Kanbara |
| 5,095,915 A | 3/1992 | Engelson |
| 5,885,207 A | 3/1999 | Iwasaka |
| 5,931,830 A | 8/1999 | Jacobsen et al. |
| 6,053,922 A | 4/2000 | Krause |
| 6,206,824 B1 | 3/2001 | Ohara |
| 6,273,876 B1 | 8/2001 | Klima |
| 6,471,640 B1 | 10/2002 | Frische |
| 6,485,411 B1 | 11/2002 | Konstorum |
| 6,682,493 B2 | 1/2004 | Mirigian |
| 6,761,686 B2 | 7/2004 | Takase |
| 7,011,627 B2 | 3/2006 | Abe |
| 7,413,563 B2 | 8/2008 | Corcoran |
| 7,579,550 B2 | 8/2009 | Dayton et al. |
| 2007/0233040 A1 | 10/2007 | Macnamara et al. |

FOREIGN PATENT DOCUMENTS

| | | |
|---|---|---|
| EP | 0 448 284 A2 | 9/1991 |
| EP | 0 778 038 A2 | 6/1997 |
| EP | 1 525 896 A2 | 4/2005 |

* cited by examiner

*Primary Examiner* — Jermie Cozart
(74) *Attorney, Agent, or Firm* — Bookoff McAndrews, PLLC

(57) ABSTRACT

Spiral-wound materials, spirals, and shafts made therefrom that have wraps with edges that may nest within one another are described. Such edges allow the spiral to achieve a smaller bending radius, meaning tighter turns and more flexibility due to the ability of adjacent wraps to nest within each other when the shaft is bent. Spirals having wraps with edges capable of nesting can be used in the medical field for devices that track anatomy, such as endoscopes, colonoscopes, catheters, and the like.

17 Claims, 11 Drawing Sheets

METHOD OF MAKING A FLEXIBLE DEVICE SHAFT WITH ANGLED SPIRAL WRAP

CROSS-REFERENCE TO RELATED APPLICATION

This application is a continuation of U.S. patent application Ser. No. 12/546,599, filed Aug. 24, 2009, now U.S. Pat. No. 8,124,876 B2 which is a continuation of U.S. patent application Ser. No. 11/396,248, filed Mar. 31, 2006, now U.S. Pat. No. 7,579,550 B2 all of which are incorporated herein by reference herein.

BACKGROUND

As an alternative to more invasive techniques, many medical procedures are now being performed with minimally invasive catheters or endoscopes. Such devices generally comprise an elongated shaft that is directed to a point of interest. The devices allow a physician to perform a desired task such as taking biopsy samples, performing a therapeutic procedure, or viewing the point of interest from a position outside the body of the patient.

Most catheters and endoscopes have a shaft that is flexible enough to navigate the bends of the human anatomy. The shaft often includes an outer sheath, a reinforcing braid, and a spiral wrap. The spiral wrap increases the column strength of the shaft as well as the crush and kink resistance of the shaft without adding substantially to the stiffness of the shaft. A spiral wrap can be viewed as a helical strip of material separated by gaps. An individual wrap is the portion of the helix making one complete revolution of 360° around the longitudinal axis of the helix. Each wrap has a leading surface edge and a trailing surface edge.

The conventional material used for a spiral wrap is metal. However, metal spiral wraps are expensive to produce because flat metal strips cannot easily be processed into a helix. Furthermore, the thin wall and wide gaps of the metal spiral make it a poor substrate for further processing. Plastics can be used for a spiral wrap, but plastics are more flexible than metals. Therefore, if a plastic is used, the plastic spiral wrap will require a greater wall thickness and more tightly spaced wraps as compared to metal to provide comparable crush and kink resistance.

A disadvantage with plastic spiral wraps is the larger spiral wall thickness combined with the more tightly spaced wraps which causes the surface edges of adjacent wraps to touch as the spiral wrap is bent. As a result of touching, individual wraps push away from each other. This shifts the neutral axis of the shaft when under bending loads and results in axis elongation of the shaft, which, in turn, causes reduced flexibility of the shaft. This reduced flexibility may interfere with accurately tracking a patient's anatomy with the shaft.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

To address the problems discussed above, embodiments of the present invention are related to a medical device including a shaft having a spiral wrap that reduces inadvertent axial elongation of the shaft during bending, which permits greater flexibility of the shaft. In one embodiment, the spiral wrap has beveled edges so that the edges may nest within one another. Nesting of adjacent wraps provides the shaft with increased flexibility by reducing elongation of the shaft and greater shaft column strength since wraps are less prone to sliding past one another. The present invention also includes the methods to make a spiral wrap.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Co-pending application titled "Flexible Endoscope with Variable Stiffness Shaft," U.S. application Ser. No. 11/396, 350, filed Mar. 31, 2006, describes spiral wraps having variable stiffness. This copending application is incorporated herein expressly by reference.

Figure 1:
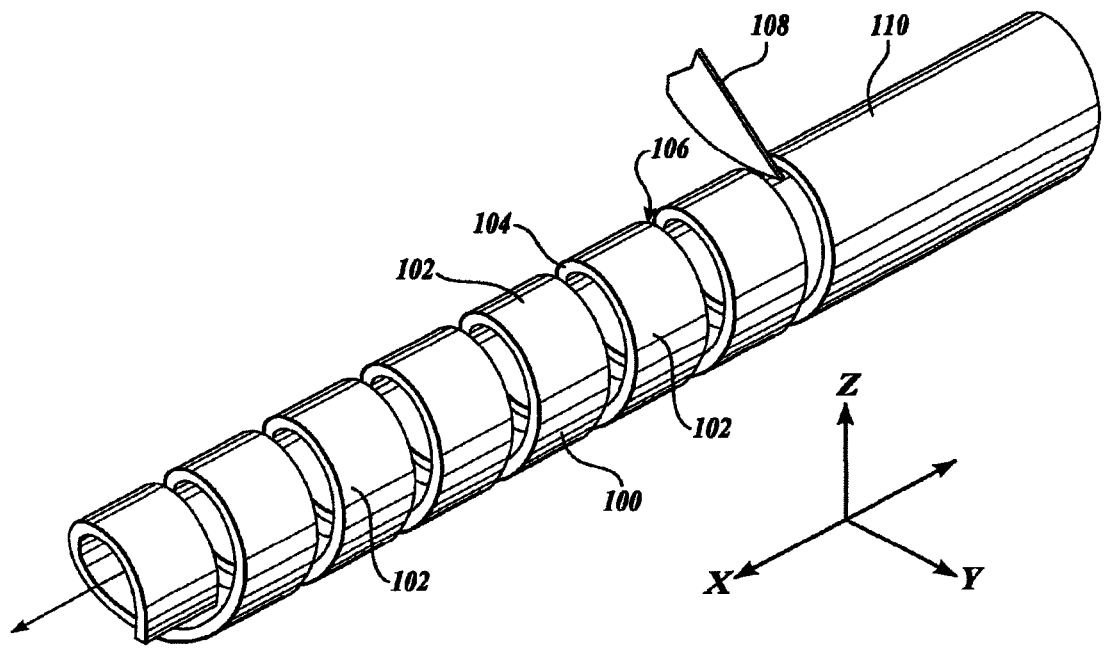
FIG. 1 is an illustration of a conventional spiral wrap being made from a plastic tube.

FIG. 1 illustrates a conventional spiral wrap 100 being cut from a plastic tube 110. The spiral wrap 100 is used as a reinforcing material in a shaft of a medical device, such as an endoscope or catheter. The spiral wrap 100 can be formed via a continuous extrusion process that first forms the cylindrical plastic tube 110. Such extrusion process pushes the tube forward, and a cutting instrument 108 is rotated around the tube 110 to cut a continuous slot in the wall of the tube 110. Because the tube 110 is moving forward, the cutting process creates a helical pattern in the tube to produce the spiral 100. Alternatively, the spiral wrap may be created by holding the tube 110 stationary and moving the cutting instrument 108 in a helical pattern while cutting the tube's 110 wall. The spiral wrap 100 can be viewed as a series of connected individual wraps, such as wraps 102. A rectangular coordinate system can be drawn where the X-axis is parallel to the central, longitudinal axis of the spiral wrap 100. The Y- and Z-axes are both perpendicular to the X-axis and to each other. The plane of the cutting instrument 108 that cuts the spiral wrap 100 from the extruded tube 110 is rotated along only one axis from a plane perpendicular to the X-axis about the Z-axis. The angle that the cutting instrument 108 makes with such a plane perpendicular to the X-axis corresponds to the angle the slot makes with the longitudinal axis of tube 110. As a result, spiral wrap 102 has a leading surface edge 104 and a trailing surface edge 106 that are composed of an infinite number of radial lines that are perpendicular to the X-axis and to the longitudinal axis of the spiral 100.

Figure 2:
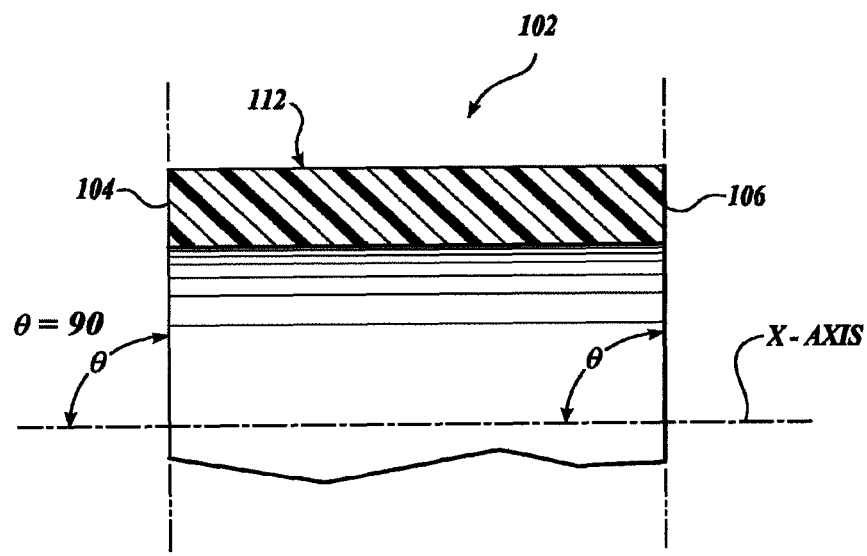
FIG. 2 is a cross-sectional illustration of a conventional spiral wrap.

Referring to FIG. 2, the cross section along any point of the single spiral wrap 102 shows the leading surface edge 104 and the trailing surface edge 106 are perpendicular to the top surface 112 of the wrap 102, which is also perpendicular to the longitudinal axis of the spiral wrap 100 of FIG. 1. A spiral having wraps with leading surface edges and trailing surface edges similar to the leading surface edge 104 and to the trailing surface edge 106, therefore, does not have wraps that can nest within another. The top surface 112 also defines the outer diameter surface of the spiral, as a whole. The angle θ is defined as the angle measured from the X-axis to the radial line defined by the leading surface edge 104 or the trailing surface edge 106. In the conventional spiral wrap, θ is equal to 90°. A spiral wrap 102 will have a limited ability to bend due to the leading surface edge 104 of one wrap coming into contact with the trailing surface edge 106 of an adjacent wrap when the edges 104 and 106 are straight.

In one embodiment of the present invention, a spiral wrap has a leading surface edge, and a trailing surface edge, that are not perpendicular to the top surface 112 or to the longitudinal axis. The angle θ of these edges can, in theory, range from an angle that is greater than 0° to less than 90°, and greater than 90° to less than 180°. Preferably, the angle θ is 30° to 60° or 120° to 150°. More preferably, the angle θ is 40° to 50° or 130° to 140°. In one configuration, the angle θ is 50° to 60°, and in one particular configuration, the angle θ is about 55°. A spiral wrap with leading and trailing edges that have an angle θ being something other than 90° are said to be beveled. In addition, as will be explained below, other examples of wraps that can nest with, cooperate with, or complement one another may not have completely planar trailing and leading edges, but can include arcuate surfaces and multi-planer surfaces.

An embodiment in accordance with the present invention is a method for forming a spiral with wraps wherein the leading surface edge and the trailing surface edge are beveled. Beveling the edges will result in adjacent wraps capable of nesting within one another when the shaft is bent to a certain degree and the edges are in close enough proximity. Furthermore, beveling the surface edges will result in a spiral capable of a smaller bending radius as compared to a spiral having non-beveled surface edges. To bevel the edges, the cutting instrument 108 can be rotated in two planes so that the plane of the cutting instrument 108 no longer cuts a slot that is composed of lines perpendicular to the X-axis, or to the top surface 112 of the wrap 102. When the cutting instrument 108 cuts a tube so that the outer surface of a leading or trailing edge of a wrap extends past the inner surface, the cut is said to be an undercut. In contrast, when the cutting instrument 108 cuts the tube so that the inner surface of a leading or trailing edge of a wrap extends past the outer surface, the cut is said to be an overcut. In accordance with an embodiment of the present invention, any leading surface edge 104 of any wrap, such as wrap 102, may be overcut or undercut. Similarly, any trailing surface edge 106 of any wrap, such as wrap 102, may be overcut or undercut.

Figure 3:
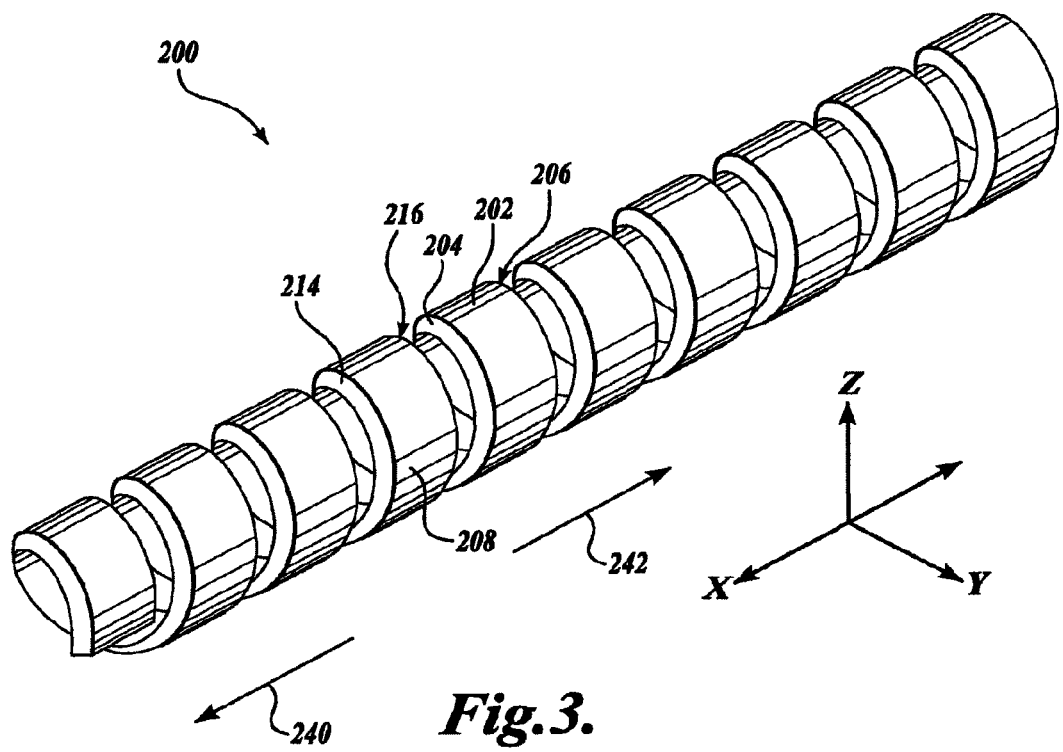
FIG. 3 is an illustration of a spiral wrap made in accordance with one embodiment of the present invention.

Referring to FIG. 3, an illustration of a spiral wrap 200 having an overcut leading edge is provided. Arrow 240 indicates the "leading" direction, while arrow 242 indicates the trailing direction in FIGS. 3-6. The spiral wrap 200 includes adjacent wraps 202 and 208 that are separated by a gap. The gap can be substantially zero or the gap can vary from zero to a predetermined amount. The overcut leading edge 204 of wrap 202 may nest within the undercut trailing edge 216 of the adjacent wrap 208. In one embodiment, "nest" or "nesting" refers to the situation where a portion of the leading surface edge of one wrap fits within a portion of the trailing surface edge of an adjacent wrap, such as by overlapping, etc. Nesting may occur when the spiral has sufficient bend, or when the spiral is compressed in the direction of the longitudinal axis. In comparison to square surface edges of the prior art, embodiments of the present invention include wraps that have complementary and/or cooperating edges, such that a portion of one edge may complement and/or cooperate with an adjacent edge to either decrease the bending radius of a spiral, or to increase the lateral strength, i.e., the resistance of the spiral to kink. Furthermore, unlike the adjacent square edges of the prior art, complementary and/or cooperating edges may also prevent the wraps from slipping past one another in the radial direction. The capability of wraps to nest while bending the spiral wrap 200 decreases the bending radius of a spiral, i.e., increases the flexibility, and results in tighter bending capability. Alternatively, the leading edge 204 may be undercut and the trailing edge 216 may be overcut. In the latter situation, the trailing edge of a forward wrap will nest within the undercut leading edge of an adjacent and rear wrap. The degree of flexibility of the spiral wrap 200 that is capable of nesting within one another is increased in comparison to the spiral wrap 100 (FIG. 1), because adjacent wraps will nest within one another instead of abutting against one another.

Figure 4:
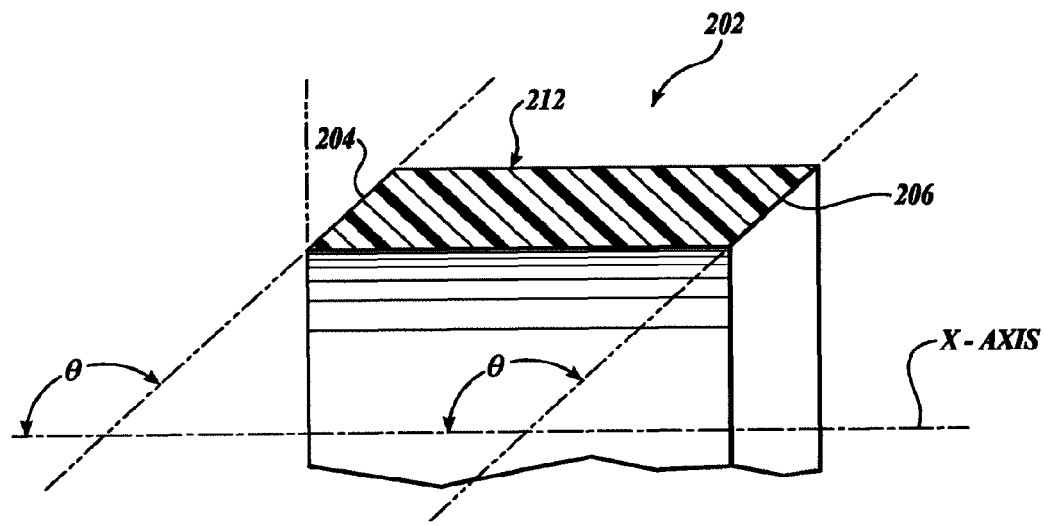
FIG. 4 is a cross-sectional illustration of a single spiral wrap shown in FIG. 3.

Referring to FIG. 4, a cross-sectional illustration of a single spiral wrap 202 is provided. The angle θ is defined by the X-axis and the radial lines on which the leading surface edge 204 and the trailing surface edge 206 lie. The angle θ can be any angle from greater than 0° to less than 90° or greater than 90° to less than 180°. When the angle θ is greater than 0°, but less than 90°, the leading surface edge 204 is undercut, and the trailing surface edge 206 is overcut. When the angle θ is greater than 90°, but less than 180°, the leading surface edge 204 is overcut, and the trailing surface edge 206 is undercut. The depth of the cut can be any thickness ranging from the full thickness of the wall measured from the outer diameter to the inner diameter, or from the inner diameter to the outer diameter. Alternatively, the depth of the cut can be less than the full thickness. Furthermore, any one, some, or all of the individual wraps in the spiral wrap 202 can be beveled. Alternatively, only a section of the spiral wrap 200 can have wraps with overcut or undercut leading surface edges and trailing surface edges. For example, sometimes it may be desired to provide the distal section of a shaft with greater flexibility (greater bending capability) as compared to the proximal section. In this situation, only wraps in the distal section can be modified to have beveled edges. The wraps of the proximal section and center section, which is between the distal section and the proximal section, are left unmodified, providing increased column strength in the proximal region (with angles closer to 90°).

Figure 5:
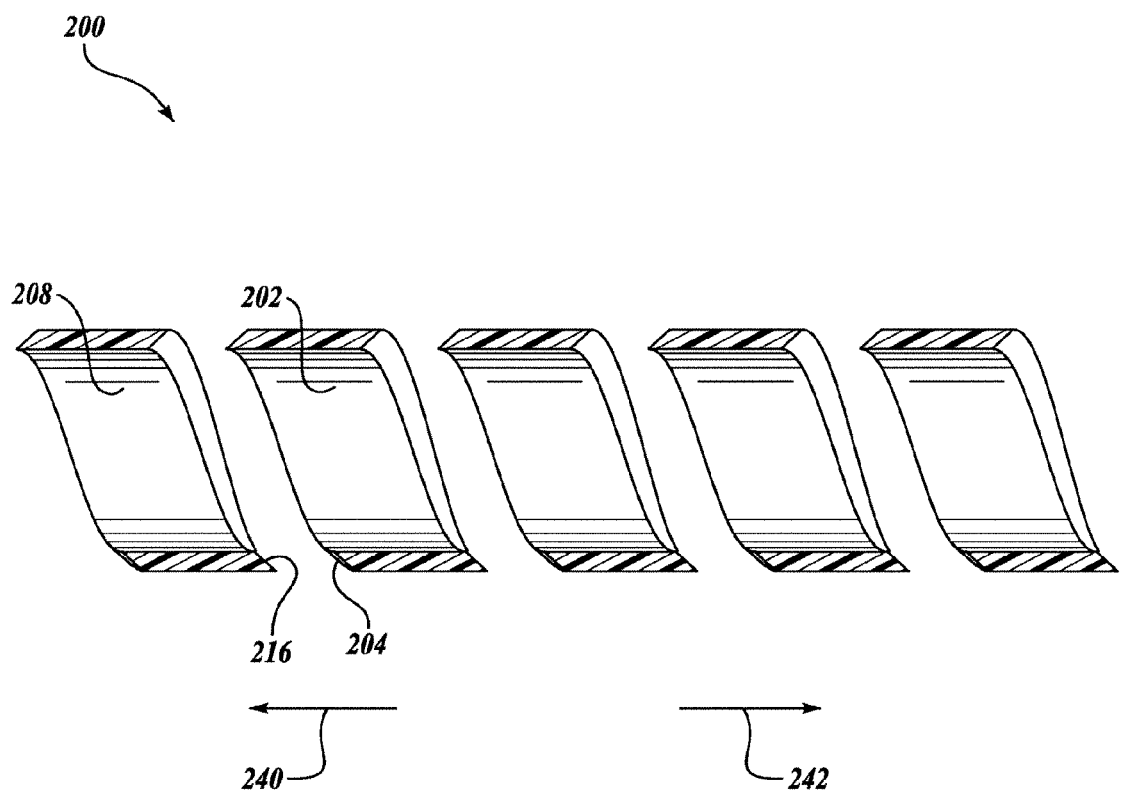
FIG. 5 is a cross-sectional illustration of multiple spiral wraps in accordance with another embodiment of the present invention.

FIG. 5 is an illustration of a cross section of the spiral wrap 200 of FIG. 3. The spiral wrap 200 includes a series of adjacent wraps, two of which are numbered 202 and 208. Wrap 202 has a leading surface edge 204. The adjacent and forward wrap 208 has a trailing surface edge 216. FIG. 5 is an illustration of the spiral 200 in the unflexed or unbent configuration. In this configuration, the leading surface edge 204 of wrap 202 is separated by a gap from the trailing surface edge 216 of wrap 208. Alternatively, the gap between wraps 202 and 208 can be substantially zero.

Figure 6A:
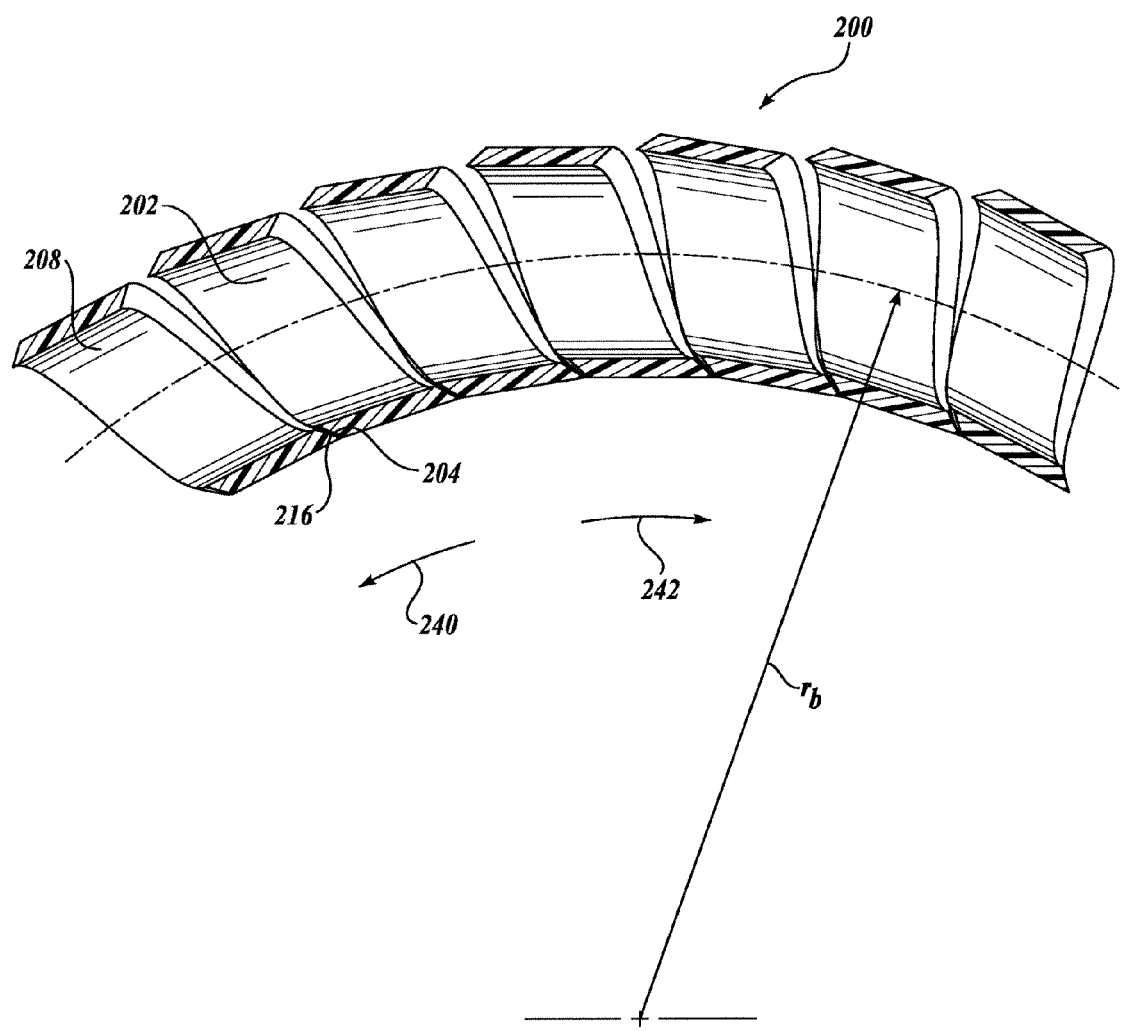
FIG. 6A is a cross-sectional illustration of a spiral wrap made in accordance with an embodiment of the present invention showing nesting of adjacent wraps.

FIG. 6A is a cross-sectional illustration of the spiral wrap 200 of FIG. 5 in the flexed or bent configuration that has reached the limit of bending without distorting the spiral material. This is an advantage when the gap between wraps is zero or close to it—with a larger gap, nesting may be unnecessary, but kinking is more likely. In the illustrated configuration, the leading surface edge 204 of wrap 202 is nested within the trailing surface edge 216 of the forward and adjacent wrap 208. Having wraps in the spiral 200, wherein the wraps contain beveled surface edges allow the individual wraps to nest within each other when the spiral is bent or flexed. Beveling the surface edges 204 and 216 of wraps 202, 208 in the spiral 200 provides the spiral 200 with a smaller bending radius ($r_b$) compared to a spiral that does not have beveled surface edges. This is because the wraps with beveled surface edges may nest within one another, increasing the ability of the shaft to bend and reducing the bending radius ($r_b$). Wraps with unbeveled or perpendicular surface edges cannot nest within one another and push away from each other when under a bending load, therefore decreasing flexibility.

Figure 6B:
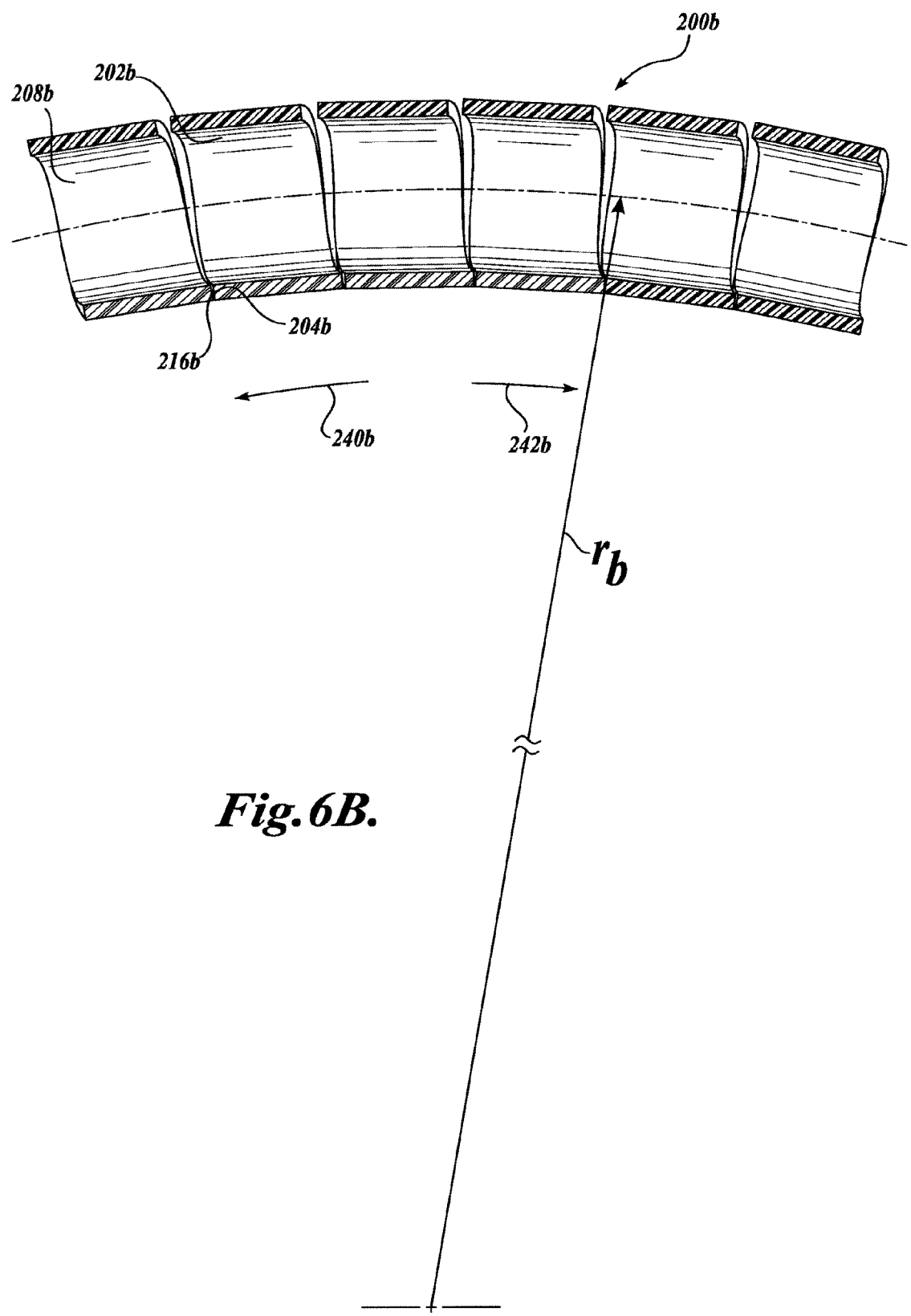
FIG. 6B is a cross-sectional illustration of a spiral wrap having straight cut edges.

Referring to FIG. 6B, a spiral wrap 200b has adjacent wraps 208b and 202b. The wrap 208b has a trailing surface edge 216b. The wrap 202b has the leading surface edge 204b. The trailing surface edge 216b and the leading surface edge 204b are cut at a 90° angle with respect to the central axis of the spiral wrap 200b. Therefore, due to the straight cut of edges 216b and 204b, the bending radius ($r_b$) is greater than the bending radius ($r_b$) of the spiral wrap 200 of FIG. 6A, all other things being equal.

Figure 7:
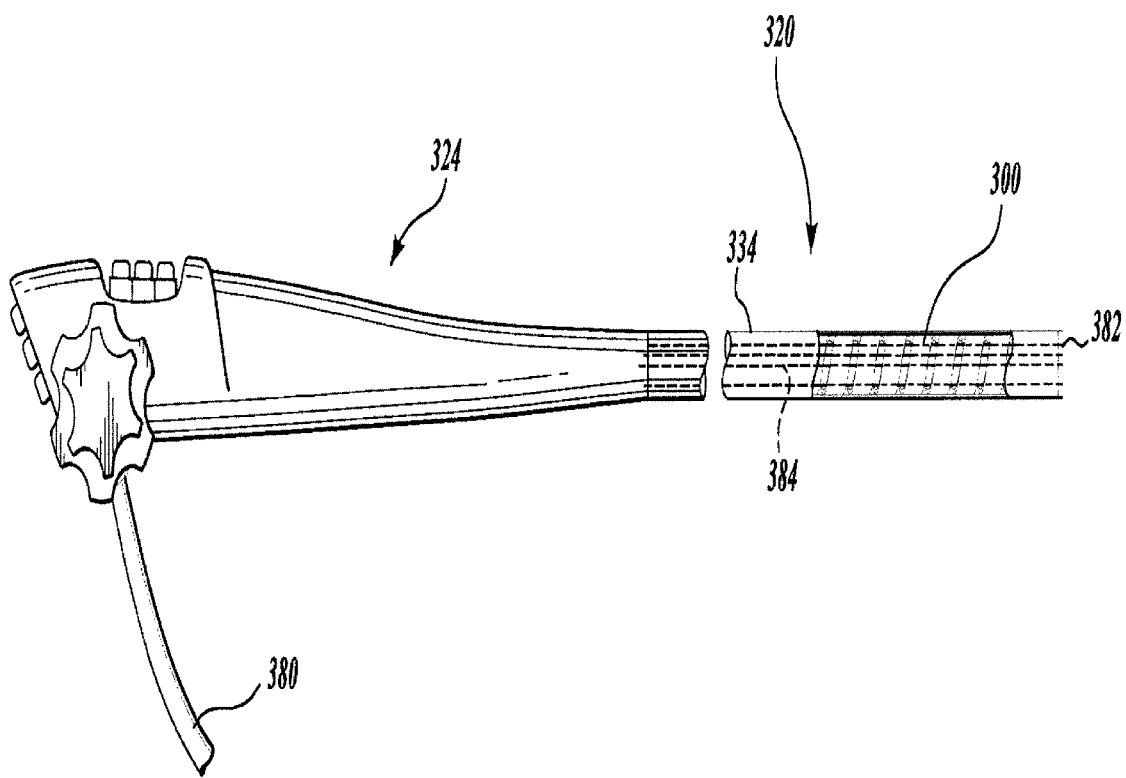
FIG. 7 is an illustration of an endoscope with a shaft having a spiral wrap made in accordance with an embodiment of the present invention.

Referring to FIG. 7, a medical device, such as an endoscope 320, is illustrated with a spiral wrap 300 formed in accordance with one embodiment of the present invention, wherein the spiral wrap 300 is surrounded with a cover sheath. The endoscope 320 includes a distal shaft 334 (insertion tube) having a spiral wrap 300. The distal shaft 334 is connected to a control handle 324, through which the endoscope 320 is controlled. The control handle 324 is connected via an umbilicus 380 to a control cabinet (not shown). The umbilicus 380 provides passageways and cables for the passing of electrical signals, current, fluids, and gasses to and from the control cabinet (not shown) to the control handle 324 and ultimately to the distal shaft 334 to be delivered to a target area in a patient. The spiral wrap 300 is a spiral made in accordance with an embodiment of the present invention. The shaft 324 includes the spiral wrap 300 and may also include a cover sheath, a metal braid, and tape, or other materials, within the shaft 334. Additionally, the distal shaft 334 of the endoscope 320 will typically have devices at the distal end that provide illumination, imaging, and steering capability, such as illumination/imaging device 382 steering cables 384, to assist with tracking the shaft 334 though the patient's anatomy. One or more electrical cables are included within the distal shaft 334 to power the illumination and imaging devices, and to carry signals to a processor to convert the signals into images that can be viewed at the control cabinet, for example. Furthermore, the distal shaft 334 of the endoscope 320 can have one or more lumens to carry liquids, gases, and devices to a target area. The additional components of shaft 334 described above are not discussed at length in this application for brevity.

Figure 8A:
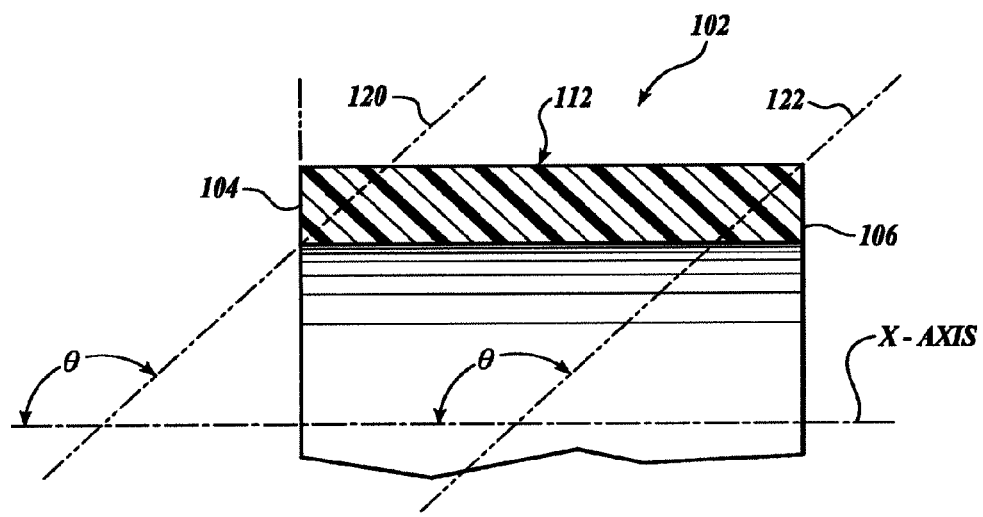
FIG. 8A is a cross-sectional illustration of a single spiral wrap to be modified in accordance with an embodiment of the present invention.
Figure 8B:
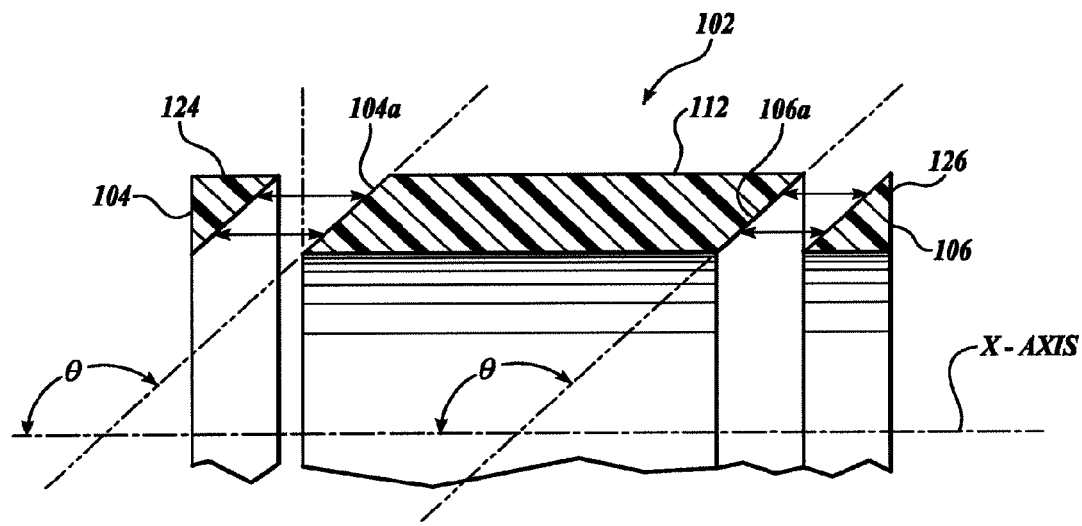
FIG. 8B is a cross-sectional illustration of a modified spiral wrap that has beveled leading and trailing surface edges in accordance with an embodiment of the present invention.

FIGS. 8A and 8B illustrate an alternate embodiment of the present invention, wherein a spiral wrap initially has individual wraps whose leading surface edge 104 and trailing surface edge 106 are generally perpendicular to the X-axis and to the longitudinal axis of the spiral. An embodiment of the present invention is a method for beveling the leading surface edge 104 and the trailing surface edge 106.

FIG. 8A is a cross-sectional illustration of a wrap 102 wherein the leading surface edge 104 and the trailing surface edge 106 have been cut perpendicular to the top surface 112 of the wrap 102, and perpendicular to the X-axis. This is the result of a first cut being made perpendicular to the top surface 112 and perpendicular to a plane that is rotated along a single axis from the X-axis, as illustrated in FIG. 1. A second and third cut may be performed on the leading surface edge 104 and the trailing surface edge 106 at the cut lines 120 and 122, respectively. Cut line 120 bevels the leading surface edge 104 into an overcut. Cut line 122 bevels the trailing surface edge 106 into an undercut.

Referring to FIG. 8B, a cross-sectional illustration of the wrap 102 after performing two additional cuts is illustrated. A second cut at the leading surface edge 104 along cut line 120 has resulted in a new leading surface edge 104a. Excess wrap material 124 may be discarded. A third cut at the trailing surface edge 106 along cut line 122 has resulted in a new trailing surface edge 106a. Excess wrap material 126 at the trailing edge may be discarded. The angle θ can be within the ranges discussed above. FIGS. 8A and 8B illustrate a method whereby multiple cuts are performed after the initial tube is formed having perpendicular edges. The method using two or three cutting operations is suited to modify existing shafts. Alternatively, if the spiral is to be newly fabricated, a single-cut method may be performed simultaneously with the tube extrusion process.

The spirals made in accordance with embodiments of the present invention can be made from any plastic and, in particular, a polyethylene, including a high-density polyethylene, or a nylon. The advantage of a plastic is the ability to fabricate spirals continuously. However, the invention is not limited to plastic materials. For example, a metal spiral can be fabricated with beveled leading and trailing surface edges. An elongated, flat strip of metal can be procured, and the parallel, longer edges beveled to the desired angle. Such beveling can include grinding the metal down to a specified angle. The metal strip can then be wound into a spiral shape on a cylindrical mandrel. The metal spiral will now have beveled leading and trailing surface edges.

A method for making the angled spiral wrap can utilize a cutting instrument. In one embodiment, a single blade can be used to cut both the trailing and leading edges of a wrap at one time. However, double knives, knives with compound edges, or knives with arcuate edges can be used to provide edges having multi-planar edges, arcuate edges, and irregular edges of the types shown in FIGS. 9A-9J.

Figure 9A:
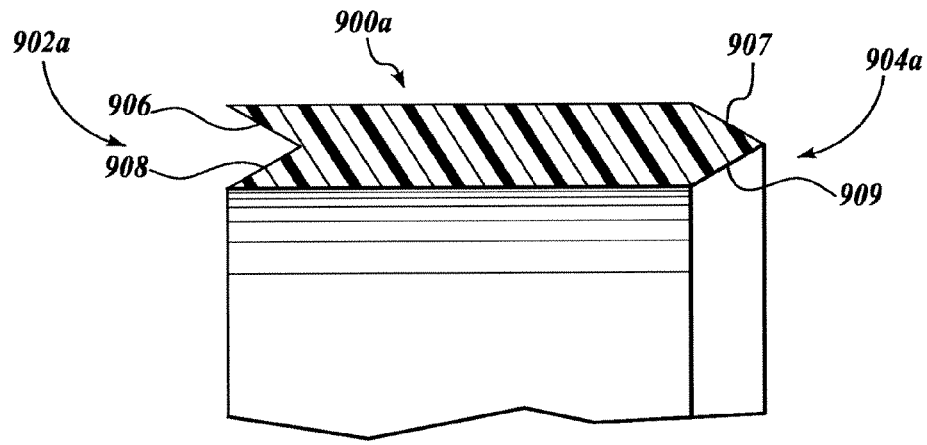
FIGS. 9A-9J are cross-sectional illustrations of single spiral wraps of additional embodiments of the present invention.

FIG. 9A is a cross-sectional illustration of an alternate embodiment of a wrap 900a made in accordance with the present invention. The wrap 900a has the leading surface edge 902a and the trailing surface edge 904a. The leading surface edge 902a has two surfaces 906 and 908. The surface 906 is an undercut that extends from the outer diameter surface towards the center of the wall thickness. The surface 908 extends from the inner diameter surface towards the center. The trailing surface edge 904a includes the surfaces 907 and 909. The surface 907 is an overcut that extends from the outer diameter surface towards the center of the wall thickness. The surface 909 is an overcut that extends from the inner diameter surface towards the center. Adjacent wraps having the profile of wrap 900a can nest within another.

Figure 9B:
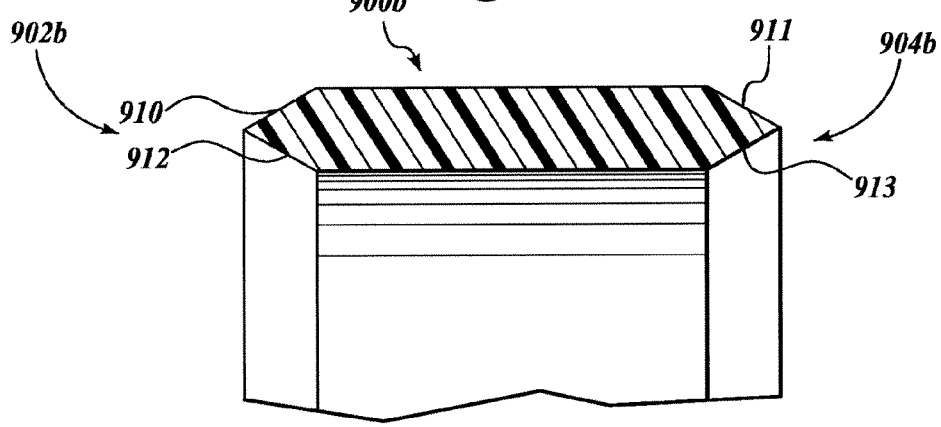

FIG. 9B is a cross-sectional illustration of an alternate embodiment of a wrap 900b made in accordance with the present invention. The wrap 900b has the leading surface edge 902b and the trailing surface edge 904b. The leading surface edge 902b includes the surfaces 910 and 912. The surface 910 is an overcut that extends from the outer diameter surface towards the center of the wall thickness. The surface 912 is an overcut that extends from the inner diameter surface towards the center of the wall thickness. The trailing surface edge 904b includes the surfaces 911 and 913. The surface 911 is an overcut that extends from the outer diameter surface towards the center of the wall thickness. The surface 913 is an overcut that extends from the inner diameter surface towards the center of the wall thickness. The wrap, as illustrated in FIG. 9B, is intended to cooperate with the wrap 900C illustrated in FIG. 9C.

Figure 9C:
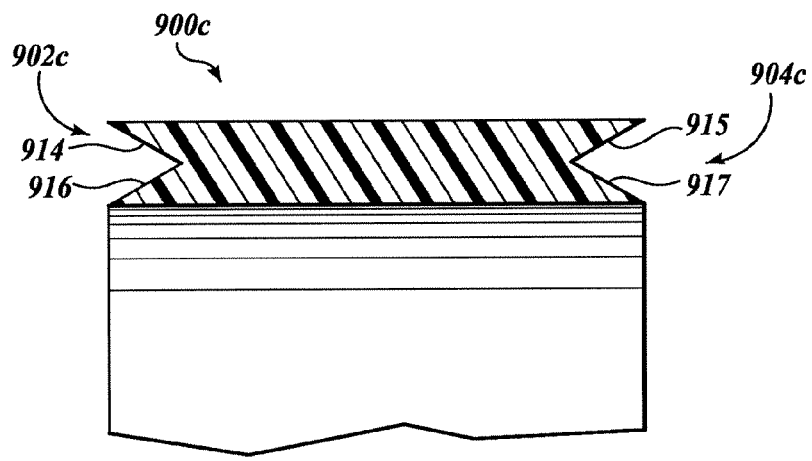

FIG. 9C is a cross-sectional illustration of an alternate embodiment of a wrap 900c made in accordance with the present invention. The wrap 900c has the leading surface edge 902c and the trailing surface edge 904c. The leading surface edge 902c includes the surfaces 914 and 916. The surface 914 is an undercut that extends from the outer diameter surface towards the center of the wall thickness. The surface 916 is an undercut that extends from the inner diameter surface towards the center of the wall thickness. The trailing surface edge 904c includes the surfaces 915 and 917. The surface 915 is an undercut that extends from the outer diameter surface towards the center of the wall thickness. The surface 917 is an undercut that extends from the inner diameter surface towards the center of the wall thickness. Wrap 900c may nest within wrap 900b, as illustrated in FIG. 9B.

Figure 9D:
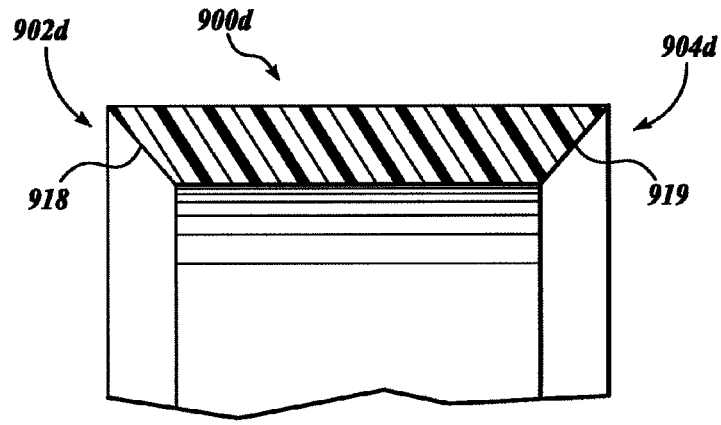

FIG. 9D is a cross-sectional illustration of an alternate embodiment of a wrap 900d made in accordance with the present invention. The wrap 900d includes the leading surface edge 902d and the trailing surface edge 904d. The leading surface edge 902d includes the surface 918. Surface 918 is an undercut that extends from the outer diameter surface towards the inner diameter surface. Surface 919 is an undercut that extends from the outer diameter surface towards the inner diameter surface. The wrap 900d is intended to cooperate with the wrap 900e illustrated in FIG. 9E, so that the leading surface edge 902d of wrap 900d nests with the trailing edge 904e of wrap 900e, for example.

Figure 9E:
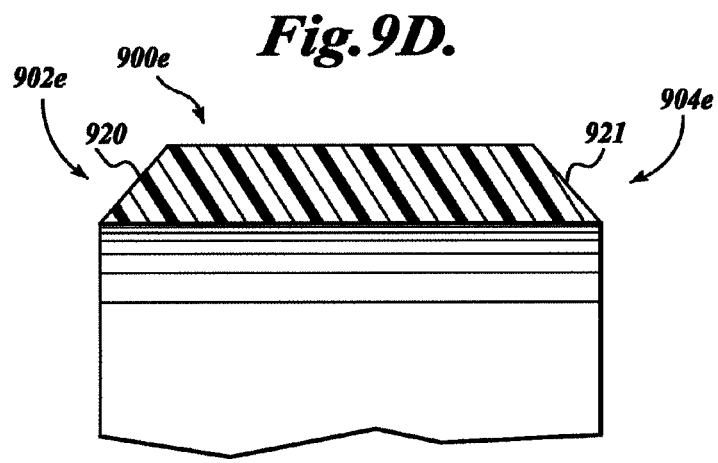

FIG. 9E is a cross-sectional illustration of an alternate embodiment of a wrap 900e made in accordance with the present invention. The wrap 900e includes the leading surface edge 902e and the trailing surface edge 904e. The leading surface edge 902e includes the surface 920. Surface 920 is an overcut that extends from the outer diameter surface towards the inner diameter surface. The trailing surface edge 904e includes the surface 921. Surface 921 is an overcut that extends from the outer diameter surface towards the inner diameter surface.

Figure 9F:
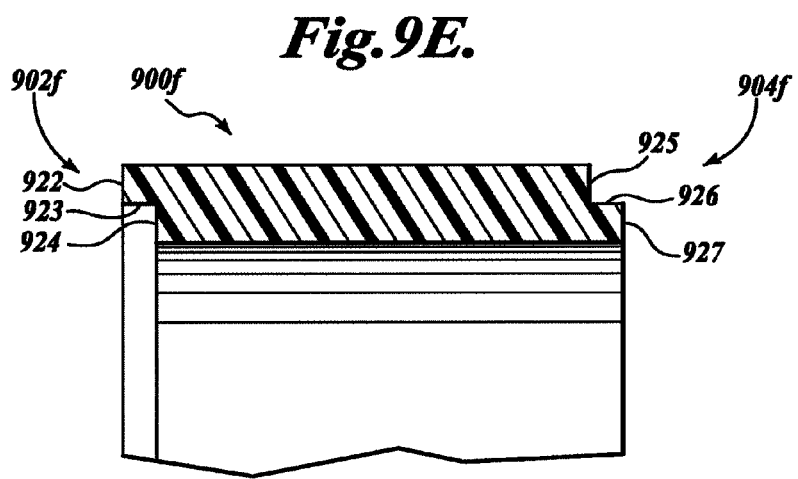

FIG. 9F is a cross-sectional illustration of an alternate embodiment of a wrap 900f made in accordance with the present invention. The wrap 900f includes the leading surface edge 902f and the trailing surface edge 904f. The leading surface edge 902f includes the surfaces 922, 923, and 924. The surface 922 is perpendicular to the outer diameter surface and extends from the outer diameter surface to the center of the wall thickness. The surface 923 is parallel to the outer diameter surface and perpendicular to the surface 922. The surface 923 extends from the end of the surface 922 towards the trailing surface edge 904f. The surface 924 is perpendicular to the outer diameter surface and to the surface 923. The surface 924 extends from the center of the wall thickness to the inner diameter surface.

The trailing surface edge 904f includes the surfaces 925, 926, and 927. Surface 925 is parallel to the surface 922 and perpendicular to the outer diameter surface. Surface 925 extends from the outer diameter surface to the center of the wall thickness. Surface 926 is parallel to the outer diameter surface and to surface 923 and perpendicular to surface 925. Surface 926 extends from the end of surface 925 towards the trailing surface edge 904f. Surface 927 is parallel to the surfaces 925 and 924 and perpendicular to the outer diameter surface and to the surface 926. Surface 927 extends from the end of surface 926 to the inner diameter surface. Adjacent wraps having the cross-sectional configuration of wrap 900f, as illustrated in FIG. 9F, will have leading surface edges that nest with trailing surface edges.

Figure 9G:
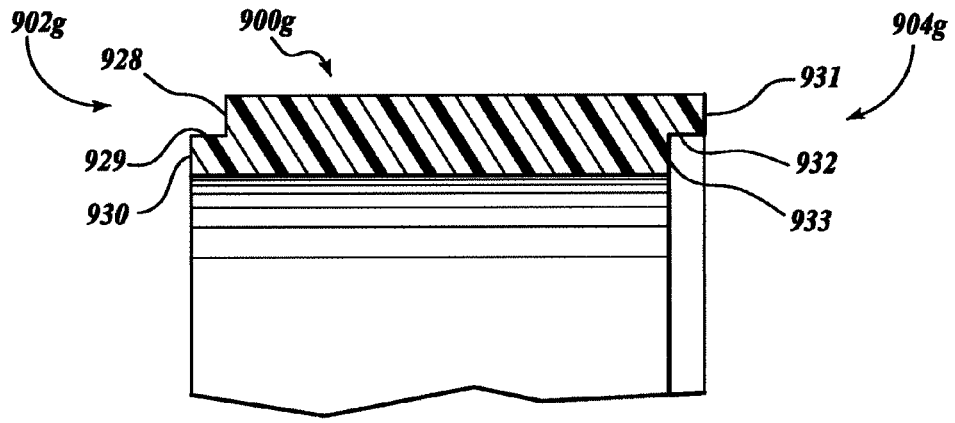

FIG. 9G is a cross-sectional illustration of an alternate embodiment of a wrap 900g made in accordance with the present invention. The wrap 900g includes the leading surface edge 902g and the trailing surface edge 904g. The leading surface edge 902g includes the surfaces 928, 929, and 930. The surface 928 is perpendicular to the outer diameter surface. The surface 928 extends from the outer diameter surface to the center of the wall thickness. The surface 929 is parallel to the outer diameter surface and perpendicular to the surface 928. The surface 929 extends from the end of the surface 928 towards the leading edge 902g. The surface 930 is parallel to the surface 928 and perpendicular to the outer diameter surface and to the surface 929. The surface 930 is parallel to the surface 928 and perpendicular to the surface 929 and to the outer diameter surface. The surface 930 extends from the end of the surface 929 towards the inner diameter surface.

The trailing surface edge 904g includes the surfaces 931, 932, and 933. The surface 931 is perpendicular to the outer diameter surface and parallel to the surface 928. The surface 931 extends from the outer diameter surface to the center of the wall thickness. The surface 932 is parallel to the outer diameter surface and to surface 929. Surface 932 is perpendicular to the surface 931. Surface 932 extends from the end of the surface 931 towards the leading surface edge 902g. The surface 933 is parallel to the surface 930 and 931. Surface 933 is perpendicular to the outer diameter surface and to the surface 932. The surface 933 extends from the end of surface 932 to the inner diameter surface. Adjacent wraps having the cross-sectional configuration of wrap 900g, as illustrated in FIG. 9g, will have leading surface edges that nest with trailing surface edges. Wrap 900g has the advantage that when nesting, adjacent wraps do not slide to the outside or to the inside of the spiral.

Figure 9H:
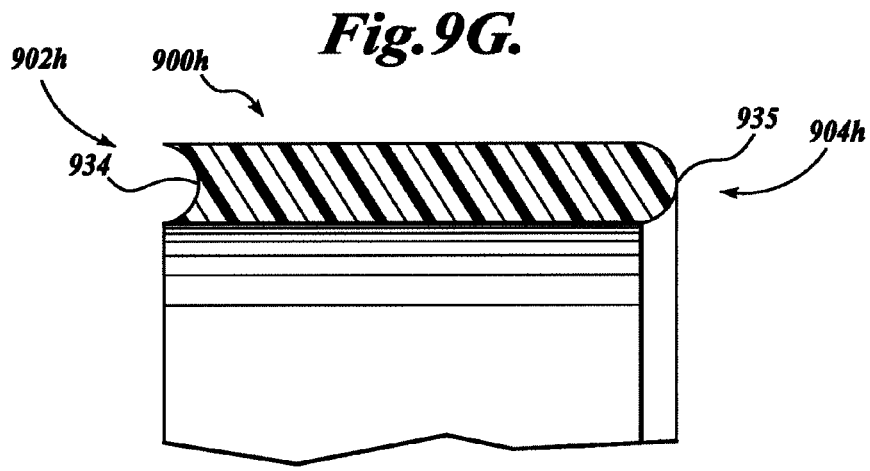

FIG. 9H is a cross-sectional illustration of an alternate embodiment of a wrap 900h made in accordance with the present invention. The wrap 900h includes the leading surface edge 902h and the trailing surface edge 904h. The leading surface edge 902h includes the surface 934. Surface 934 is a concave surface extending from the outer diameter surface to the inner diameter surface. The trailing surface edge 904h includes the surface 935. Surface 935 is a convex surface extending from the outer diameter surface to the inner diameter surface. Alternatively, leading surface edge 902h can have a convex surface and trailing surface edge 904h can have a concave surface. Adjacent wraps having the cross-sectional configuration of wrap 900h, as illustrated in FIG. 9H, will have leading surface edges that nest with trailing surface edges.

Figure 9I:
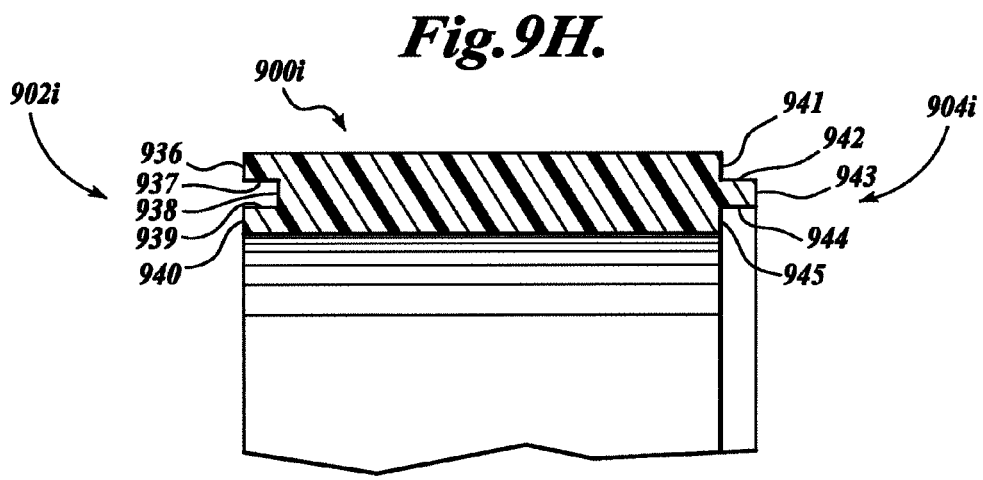

FIG. 9I is a cross-sectional illustration of an alternate embodiment of a wrap 900i made in accordance with the present invention. The wrap 900i includes the leading surface edge 902i and the trailing surface edge 904i. The leading surface edge 902i includes the surfaces 936, 937, 938, 939, and 940. Surface 936 is perpendicular to the outer diameter surface and extends to one-third of the wall thickness from the outer diameter surface. Surface 937 is perpendicular to the surface 936 and extends from the end of surface 936 towards the trailing surface edge 904i. Surface 938 is parallel to surface 936 and perpendicular to surface 937. Surface 938 extends from the end of surface 937 to two-thirds the wall thickness measured from the outer diameter surface. Surface 939 is parallel to surface 937 and perpendicular to surface 938 and 936. Surface 939 extends from the end of surface 938 towards the leading surface edge 902i. Surface 940 is parallel to surfaces 938 and 936 and perpendicular to surfaces 939, 937 and to the outer diameter surface. Surface 940 extends from the end of surface 939 to the inner diameter surface.

The trailing surface edge 904i includes the surfaces 941, 942, 943, 944, and 945. Surface 941 is perpendicular to the outer diameter surface and parallel to surface 936. Surface 941 extends from the outer diameter surface to one-third the wall thickness measured from the outer diameter surface. Surface 942 is parallel to the outer diameter surface and perpendicular to surface 941. Surface 942 extends from the end of surface 941 towards the trailing surface edge 904i. Surface 943 is parallel to surface 941 and perpendicular to surface 942 and to the outer diameter surface. Surface 943 extends from the end of surface 942 to two-thirds the wall thickness measured from the outer diameter surface. Surface 944 is parallel to the surface 942 and to the outer diameter surface, and perpendicular to the surfaces 943 and 941. Surface 944 extends from the end of surface 943 towards the leading edge 902i. Surface 945 is perpendicular to surfaces 944 and 942 and parallel to surfaces 943 and 941. Surface 945 extends from the end of surface 944 to the inner diameter surface. Surface 945 extends from two-thirds the wall thickness measured from the outer diameter surface towards the inner surface. Adjacent wraps having the cross-sectional configuration of wrap 900i, as illustrated in FIG. 9I, will have leading surface edges that nest with trailing surface edges.

Figure 9J:
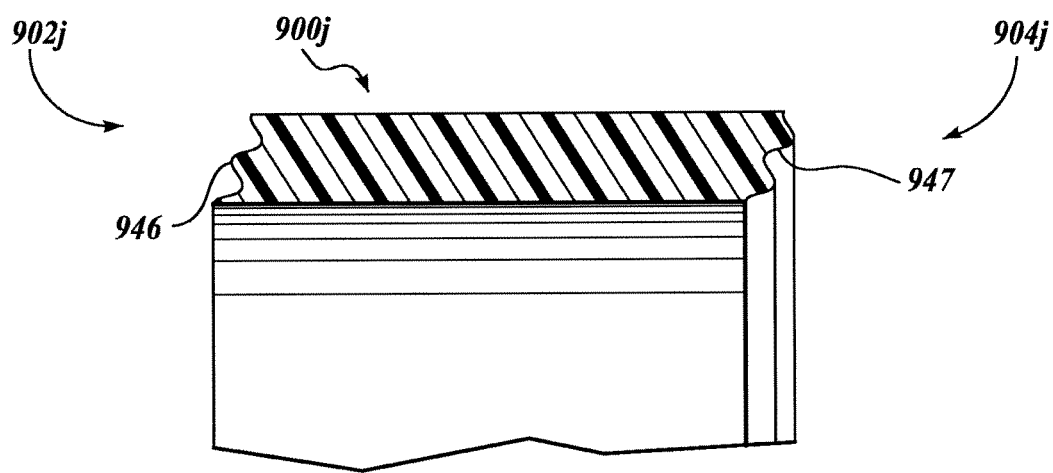

FIG. 9J is a cross-sectional illustration of an alternate embodiment of a wrap 900j made in accordance with the present invention. The wrap 900j includes the leading surface edge 902j and the trailing surface edge 904j. The leading surface edge 902j has the scalloped edge 946. The trailing surface edge 904j has the scalloped edge 947. Scalloped edges 946 and 947 have multiple arcuate surfaces being alternately concave and convex along a trailing or leading surface edge of a single wrap. Adjacent wraps having the cross-sectional configuration of wrap 900j, as illustrated in FIG. 9J, will have leading surface edges that nest with trailing surface edges.

Materials for construction of a spiral include plastics, metals, ceramics, or any combination thereof. Further, shafts with spirals having wraps with beveled edges and/or nesting edges are not limited to the medical field. Any shaft structure that uses a spiral and is required to bend may benefit from the above-described modifications. Such alternate fields of use include the materials handling field that uses equipment to convey fuel, cement, or sand, for example.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for making a shaft of a medical device, comprising:
    cutting an elongate tube to produce a spiral comprising a series of adjacent wraps, wherein each wrap of the series of adjacent wraps includes a radially inner diameter surface, a radially outer diameter surface, a leading surface edge face and a trailing surface edge face, and wherein a leading surface edge face of a first wrap nests with a trailing surface edge face of an adjacent second wrap; and
    assembling the spiral with medical device components to form a shaft of a medical device;
    wherein a cross-sectional shape extending between the radially inner diameter surface and the radially outer diameter surface of at least one of the leading surface edge face and the trailing surface edge face of a wrap of the series of adjacent wraps is defined by an arcuate surface.

2. The method of claim 1, further including:
    extruding the tube.

3. The method of claim 2, wherein the cutting and the extruding are performed simultaneously.

4. The method of claim 1, wherein the cutting includes rotating a cutting instrument about the tube along a plane that is non-perpendicular to a longitudinal axis of the tube.

5. The method of claim 1, wherein a cross-sectional shape of both of the leading surface edge face and the trailing surface edge face is defined by an arcuate surface, wherein the arcuate surface of the leading surface edge face is at least one of a concave surface and a convex surface, and wherein the arcuate surface of the trailing surface edge face is the other of the at least one of the concave surface and the convex surface.

6. A method for making a shaft of a medical device, comprising:
    rotating at least one of a cutting instrument and an elongate tube relative to the other of the cutting instrument and the elongate tube so as to cut the elongate tube to produce a spiral, wherein the spiral comprises a series of adjacent wraps, wherein each wrap of the series of adjacent wraps includes a radially inner diameter surface, a radially outer diameter surface, a leading surface edge face and a trailing surface edge face, and wherein a leading surface edge face of a first wrap nests with a trailing surface edge face of an adjacent second wrap; and
    assembling the spiral with medical device components to form a shaft of a medical device;
    wherein a cross-sectional shape extending between the radially inner diameter surface and the radially outer diameter surface of at least one of the leading surface edge face and the trailing surface edge face of a wrap of the series of adjacent wraps is defined by a plurality of planar surfaces.

7. The method of claim 6, further including:
    extruding the elongate tube, wherein the extruding and the rotating are performed simultaneously.

8. The method of claim 6, wherein the rotating includes:
    rotating the elongate tube relative to the cutting instrument.

9. The method of claim 6, wherein the rotating includes:
    rotating the cutting instrument relative to the elongate tube.

10. The method of claim 6, wherein the cutting instrument includes at least one of a single knife blade, a double knife blade, a compound edge knife blade, and an arcuate edge knife blade.

11. The method of claim 6, wherein the rotating includes rotating the cutting instrument about the tube along a first plane that is non-perpendicular to the longitudinal axis and about a second plane that is non-perpendicular to the longitudinal axis and different than the first plane so as to form a beveled leading surface edge face and a beveled trailing surfaces edge face.

12. The method of claim 6, wherein the plurality of planar surfaces includes at least a first surface extending along a plane that is parallel to the longitudinal axis, a second surface extending along a plane that is perpendicular to the longitudinal axis, and a third surface extending along a plane that is perpendicular to the longitudinal axis.

13. A method for making a shaft of a medical device, comprising:
rotating at least one of a cutting instrument and an elongate tube relative to the other of the cutting instrument and the elongate tube so as to cut the elongate tube along a plane that is non-perpendicular to a longitudinal axis of the tube to produce a spiral, wherein the spiral comprises a series of adjacent wraps, wherein each wrap of the series of adjacent wraps includes a leading surface edge and a trailing surface edge, and wherein a leading surface edge of a first wrap nests with a trailing surface edge of an adjacent second wrap; and
assembling the spiral with medical device components to form a shaft of a medical device;
wherein the rotating includes rotating the cutting instrument about the tube along a first plane that is non-perpendicular to the longitudinal axis and about a second plane that is non-perpendicular to the longitudinal axis and different than the first plane so as to form a beveled leading surface edge and a beveled trailing surface edge.

14. The method of claim 13, wherein at least one of the leading surface edge and the trailing surface edge includes a first surface comprising an angled undercut extending from an outer diameter surface of the tube towards the longitudinal axis, and a second surface comprising an angled undercut extending from an inner diameter surface of the tube towards the longitudinal axis.

15. The method of claim 14, wherein the other of the leading surface edge and the trailing surface edge includes a first surface comprising an angled overcut extending from an outer diameter surface of the tube towards the longitudinal axis, and a second surface comprising an angled overcut extending from an inner diameter surface of the tube towards the longitudinal axis.

16. The method of claim 14, wherein the other of the leading surface edge and the trailing surface edge includes a first surface comprising an angled undercut extending from an outer diameter surface of the tube towards the longitudinal axis, and a second surface comprising an angled undercut extending from an inner diameter surface of the tube towards the longitudinal axis.

17. The method of claim 13, wherein both of the leading surface edge and the trailing surface edge include a first surface comprising an angled overcut extending from an outer diameter surface of the tube towards the longitudinal axis, and a second surface comprising an angled overcut extending from an inner diameter surface of the tube towards the longitudinal axis.

* * * * *